United States Patent
Kovach

(10) Patent No.: US 9,999,425 B2
(45) Date of Patent: Jun. 19, 2018

(54) MITRAL VALVE LEAFLET CLIP

(71) Applicant: St. Jude Medical, Cardiology Division, Inc., St. Paul, MN (US)

(72) Inventor: Melinda K. Kovach, Plymouth, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 340 days.

(21) Appl. No.: 14/205,828

(22) Filed: Mar. 12, 2014

(65) Prior Publication Data

US 2014/0276971 A1 Sep. 18, 2014

Related U.S. Application Data

(60) Provisional application No. 61/788,524, filed on Mar. 15, 2013, provisional application No. 61/778,643, filed on Mar. 13, 2013.

(51) Int. Cl.
*A61B 17/10* (2006.01)
*A61B 17/08* (2006.01)
(Continued)

(52) U.S. Cl.
CPC .......... *A61B 17/083* (2013.01); *A61B 17/064* (2013.01); *A61B 17/068* (2013.01);
(Continued)

(58) Field of Classification Search
CPC ....... A61B 17/08; A61B 17/083; A61B 17/10; A61B 17/115; A61B 17/1152; A61B 17/12; A61B 17/122; A61B 17/1227; A61B 2017/081; A61B 2017/086; A61B 2017/1103; A61B 2017/1107; A61B 2017/1121; A61B 2017/00584; A61B 2017/00592; A61B 2017/00637; A61B 2017/0061; A61B 2017/00668; A61B 2017/00659; A61B 17/064; A61B 17/0642; A61B 17/0643; A61B 17/0644; A61B 17/076; A61B 17/088; A61B 17/1222;
(Continued)

(56) References Cited

U.S. PATENT DOCUMENTS 6,231,581 B1 * 5/2001 Shank .................. A61B 17/064 606/157
7,485,124 B2 * 2/2009 Kuhns .................. A61B 17/064 606/151

(Continued)

OTHER PUBLICATIONS

"Curve." Oxford Dictionaries, n.d. Web. Mar. 1, 2016 <http://www.oxforddictionaries.com/us/definition/american_english/curve>.*

*Primary Examiner* — Katrina Stransky
*Assistant Examiner* — Kankindi Rwego
(74) *Attorney, Agent, or Firm* — Lerner, David, Littenberg, Krumholz & Mentlik, LLP

(57) ABSTRACT

A clip used to repair the tissue of a heart valve leaflet may include a shaft having a barb and a plurality of legs connected to the shaft. The plurality of legs may extend away from the barb in a first condition, and may extend towards the barb in a use condition. The clips may be delivered to the heart valve leaflet and applied to the same in a minimally invasive procedure using a transcatheter device. The device may be used to apply a single clip to the leaflet tissue or multiple clips.

20 Claims, 13 Drawing Sheets

(51) Int. Cl.
*A61F 2/24* (2006.01)
*A61B 17/064* (2006.01)
*A61B 17/068* (2006.01)
*A61B 17/122* (2006.01)
*A61B 17/00* (2006.01)

(52) U.S. Cl.
CPC .......... *A61B 17/1227* (2013.01); *A61F 2/246* (2013.01); *A61F 2/2466* (2013.01); *A61B 2017/00243* (2013.01); *A61B 2017/00349* (2013.01); *A61B 2017/0641* (2013.01); *A61B 2017/0645* (2013.01); *A61F 2220/0016* (2013.01)

(58) Field of Classification Search
CPC .............. A61B 17/1225; A61B 17/128; A61B 17/1285; A61B 17/32056; A61B 2017/0641; A61B 2017/0645; A61B 2017/0646; A61B 2017/0647; A61B 2017/0648; A61B 2017/0649; A61F 6/20; A61F 6/202; A61F 6/204; A61F 6/206; A61F 6/208; A61F 6/22; A61F 6/225; A61F 6/24; A61F 2/2454; A61F 2/2457; A61F 2/246; A61F 2/2463; A61F 2/2466
See application file for complete search history.

(56) References Cited

U.S. PATENT DOCUMENTS

| | | | |
|---|---|---|---|
| 2005/0080454 A1* | 4/2005 | Drews | A61B 17/064 606/221 |
| 2007/0093857 A1* | 4/2007 | Rogers | A61B 17/0644 606/142 |
| 2008/0065152 A1* | 3/2008 | Carley | A61B 17/0644 606/215 |
| 2008/0281411 A1* | 11/2008 | Berreklouw | A61B 17/11 623/2.11 |
| 2009/0054805 A1* | 2/2009 | Boyle, Jr. | A61B 10/0266 600/564 |
| 2012/0180799 A1* | 7/2012 | Pflueger | A61F 5/566 128/848 |

* cited by examiner

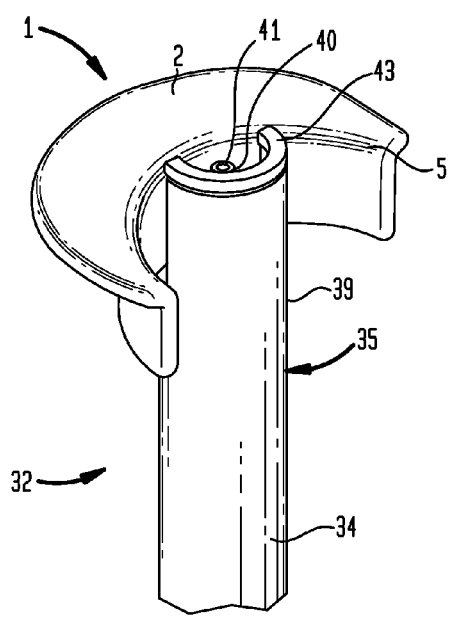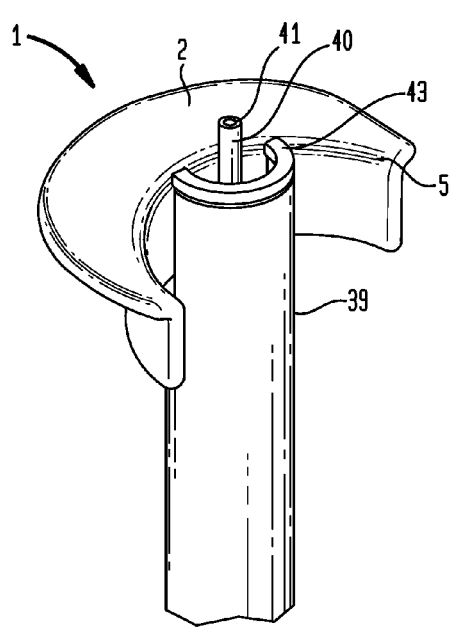

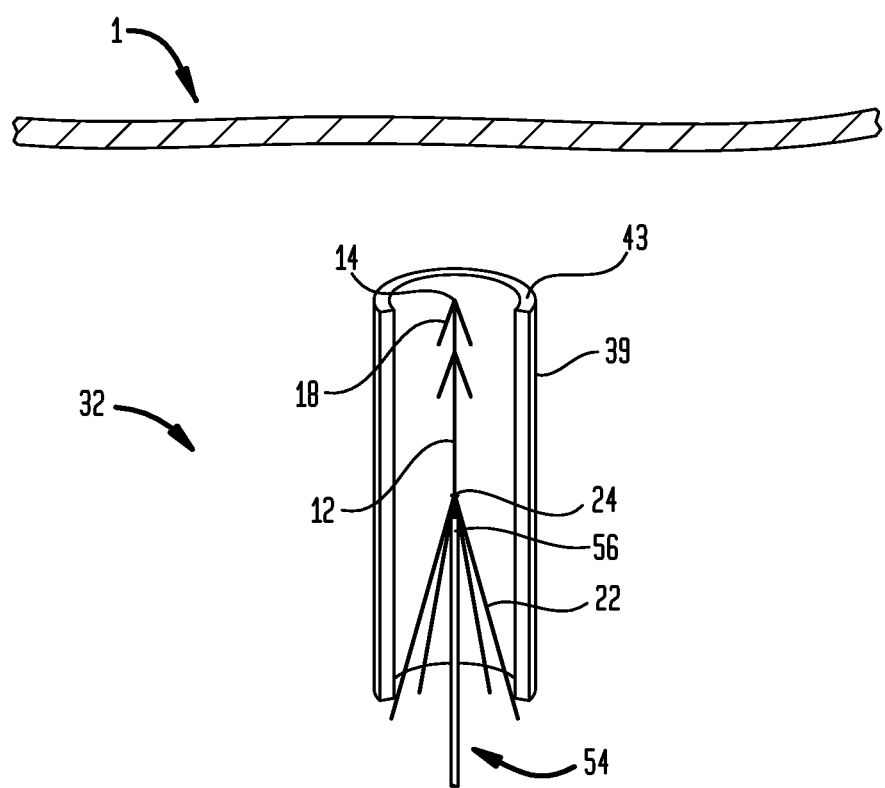

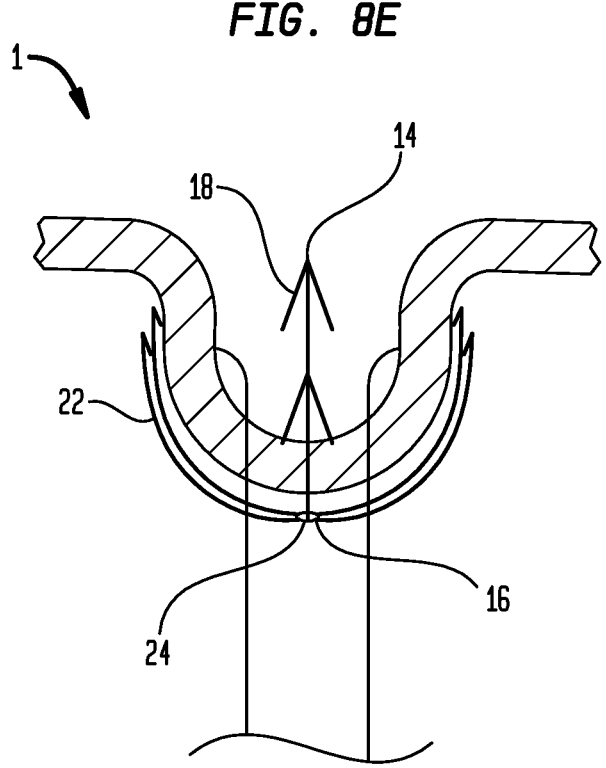

MITRAL VALVE LEAFLET CLIP

CROSS-REFERENCE TO RELATED APPLICATIONS

The present application claims the benefit of the filing date of U.S. Provisional Patent Application Nos. 61/778,643 and 61/788,524, each titled "Mitral Valve Leaflet Clip" and filed on Mar. 13, 2013 and Mar. 15, 2013, respectively, the disclosures of which are incorporated by reference herein.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be broken. As a result, the valve does not close normally, and the unsupported valve leaflet may bulge back, or "prolapse," into the left atrium like a parachute. Thus, as the ventricle contracts, the abnormal leaflet may be propelled backwards, beyond its normal closure line into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, some methods of treating mitral valve prolapse include replacement of the mitral valve, and/or resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

A first aspect of the invention includes a clip for attachment to tissue of a heart valve leaflet, the clip comprising a shaft having first and second ends, a sharpened tip on the first end of the shaft, and a plurality of legs, each leg having one end connected to the shaft at a point of connection spaced from the sharpened tip and a free end, the plurality of legs being biased to contract from an at least partially open condition to a use condition for application to the leaflet tissue. In one embodiment, the plurality of legs are at least partially formed of a shape memory material, and a barb is disposed on the shaft of the clip. A plane may also extend though the shaft, and the plurality of legs may be connected to the shaft such that an equal number of legs are disposed on each side of the plane. The use condition may also correspond to a condition in which at least one of the legs points in a direction towards the sharpened tip of the shaft.

A second aspect of the invention is a system for attaching a clip to tissue of a heart valve leaflet, the system comprising a delivery device including a catheter assembly extending in a longitudinal direction, and a clip contained in the delivery device for attachment to the leaflet tissue. The clip, in some variants, comprises a shaft having first and second ends, a sharpened tip on the first end of the shaft, and a plurality of legs, each leg having one end connected to the shaft at a point of connection spaced from the sharpened tip and a free end. According to the second aspect, the clip may also be restrained in the delivery device in an at least partially open condition, and be biased to contract to a use condition upon deployment from the delivery device. The system may also comprise a capture tool slidable in the catheter assembly between a retracted position and an extended position, the capture tool including a grasping member operable to grasp the leaflet tissue.

A third aspect of the invention includes a transcatheter method of gathering tissue, the method comprising inserting an elongated catheter assembly to a position adjacent the tissue, the catheter assembly extending in a longitudinal direction and including a capture tool and a clip, the capture tool being moveable between a retracted position and an extended position in which a portion of the capture tool protrudes from a distal end of the catheter assembly. In some embodiments of the method, the clip includes a shaft having first and second ends, a sharpened tip on the first end of the shaft, and a plurality of legs, each leg having one end connected to the shaft at a point of connection spaced from the sharpened tip and a free end. The method may also comprise the steps of: (1) moving the capture tool from the retracted position to the extended position; (2) engaging the capture tool with the tissue; and (3) deploying the clip from the distal end of the catheter assembly, whereupon the sharpened tip punctures the tissue and the plurality of legs move from an at least partially open condition to a use condition about the tissue. While several of the aforementioned steps are situated in a particular order, it is to be understood that the order is not necessarily as presented.

In one embodiment of the third aspect, the capture tool also includes a grasping wire slidably disposed in a containment tube, and the method further comprises sliding a distal portion of the grasping wire out from the containment tube so that the distal portion of the grasping wire changes from a substantially linear shape to a hook shape.

BRIEF DESCRIPTION OF THE DRAWINGS

Various embodiments of the present inventions will now be discussed with reference to the appended drawings. It is appreciated that these drawings depict only some embodiments of the inventions and are therefore not to be considered limiting of its scope.

FIG. 3a is a perspective view of the distal portion of one embodiment of a device for transcatheter gathering of heart valve leaflet tissue, engaged with the posterior leaflet of a mitral valve.

FIG. 3b is a perspective view of the distal portion of the device of FIG. 3a, shown with the containment tube deployed.

FIG. 5a is a perspective view of one embodiment of a handle suitable for controlling the device of FIG. 3a, shown with the buttons positioned to correspond to the positions of the components of the device shown in FIG. 3a.

FIG. 6 is a longitudinal cross-sectional view showing one embodiment of a clip positioned within the distal portion of the device shown in FIG. 3a.

FIG. 7b is a perspective view of the handle of FIG. 5a, shown with the buttons positioned to correspond to the positions of the components of the device shown in FIG. 7a.

FIGS. 8a-e are longitudinal cross-sectional views showing the use of the device of FIG. 3a (although slightly modified) to apply a clip to a mitral valve leaflet.

FIG. 9a is a top view of one embodiment of a clip used to repair a mitral valve leaflet, while

DETAILED DESCRIPTION

In describing preferred embodiments of the present inventions, specific terminology will be used for the sake of clarity. However, the inventions are not intended to be limited to any specific terms used herein, and it is to be understood that each specific term includes all technical equivalents that operate in a similar manner to accomplish a similar purpose.

As used herein, the terms "proximal" and "distal" are to be taken as relative to a user (e.g., a surgeon or an interventional cardiologist) using the disclosed clips and transcatheter devices. "Proximal" is to be understood as relatively closer to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
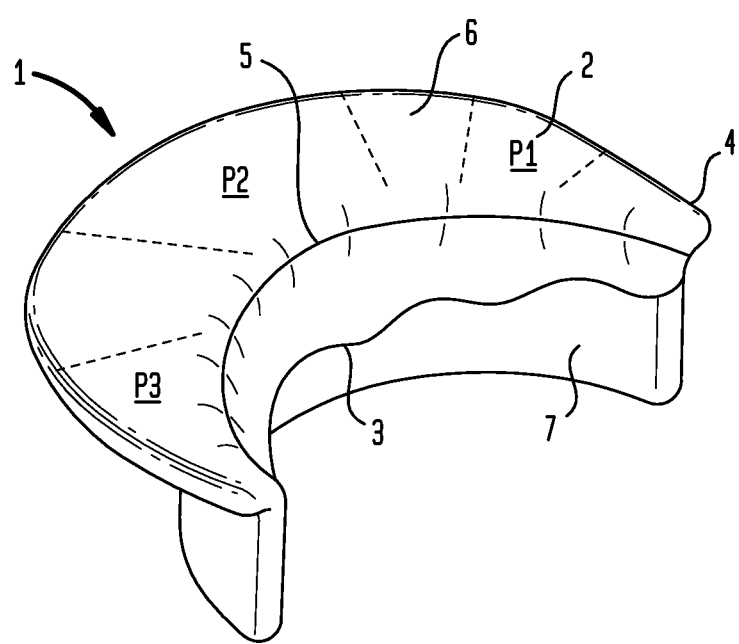
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of the posterior leaflet 2 or the anterior leaflet 3.

Figure 2A:
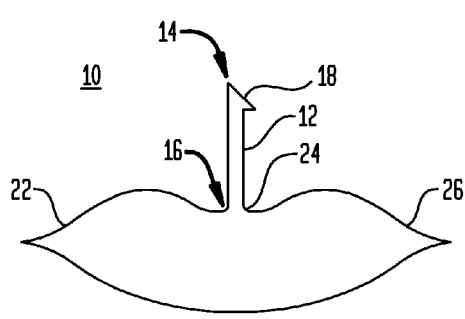
FIGS. 2a-f are top plan views of various embodiments of a clip used to repair a mitral valve leaflet.
Figure 2B:
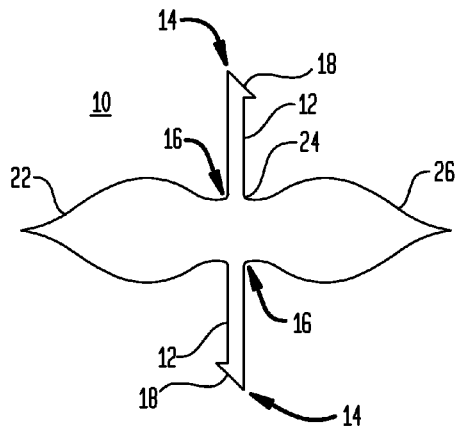
Figure 2C:
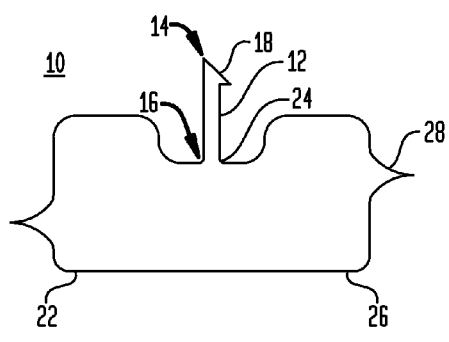
Figure 2D:
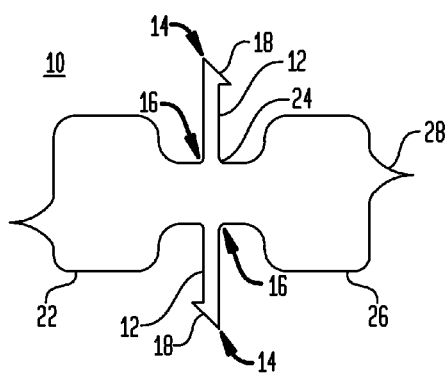

Referring to FIGS. 2a-f, several embodiments of clips 10 are shown, the clips 10 being used to tighten and repair a billowed, loose, or floppy portion of human tissue, such as the posterior leaflet 2 of mitral valve 1. FIGS. 2a-f in particular depict clips 10 as they appear when cut from a flat sheet of material (e.g., through laser cutting, chemical etching, stamping or other like processes), and not as they necessarily would appear in their final form, such as when deployed in the body of a patient. Indeed, FIGS. 10a-f depict certain of clips (e.g., clips 10 as shown in FIGS. 2c-d) in their deployed or near-deployed state. In any case, as shown in FIGS. 2a-f, each of clips 10 may include at least one shaft 12 having a first end 14 and a second end 16. A barb 18 may be provided on the first end 14 of the shaft 12 for puncturing and hooking into the mitral valve tissue being repaired. At its second end 16, the shaft 12 may have a plurality of legs 22 for grasping and tightening the leaflet tissue.

Figure 2E:
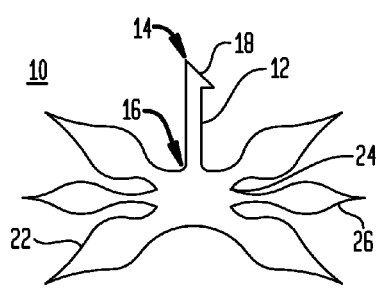
Figure 2F:
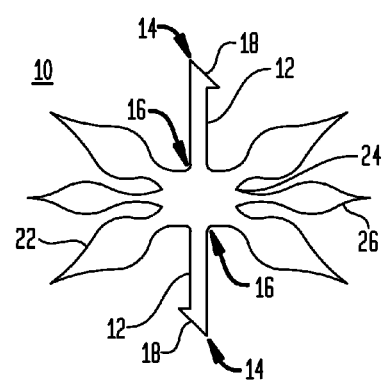

The clips 10 may have a single shaft 12 or multiple shafts, each shaft having a first end 14 and a second end 16. FIGS. 2a, 2c, and 2e depict clips 10 having a single shaft 12, while FIGS. 2b, 2d, and 2f depict clips having two shafts. Where clips 10 have multiple shafts 12, each shaft may include a barb 18 on the first end 14 thereof for puncturing into and grasping sections of damaged mitral valve tissue, and a plurality of legs 22 at its second end 16 for grasping and tightening the leaflet tissue.

Shafts 12 may have a length that corresponds to the maximum thickness of the damaged valve tissue to be punctured by the barb 18. In other words, each shaft 12 may have a length extending from the first end 14 to the second end 16 such that the barb 18 may puncture the damaged mitral valve tissue 1 from one side through to the other side, but not extend further than is necessary. The length of shafts 12 is not critical, however, and may be greater than the thickness of the damaged mitral valve tissue being repaired.

Each of legs 22 may connect to a shaft 12 at a point of connection 24 spaced from the barb 18, and may extend away from the shaft to a free end 26. The point of connection 24 may be at the second end 16 of the shaft 12, although alternate points of connection are also contemplated. For example, one or all of the legs 22 may have a point of connection 24 with the shaft 12 between the first end 14 and the second end 16 of the shaft. Moreover, each leg 22 may have the same or a different point of connection 24 with shaft 12, or some of the legs may share a single point of connection, while there may be one or more other points of connection for the remaining legs. The free end 26 of one or more of the legs 22 may be spaced from the point of connection 24 and remain unconnected to the shaft 12, such that the one or more legs 22 are free to be deformed or bent in a particular direction.

The plurality of legs 22 may also be positioned on the shaft 12 such that an equal number of legs are situated on each side of a plane extending through the shaft. Furthermore, each leg 22 on a particular side of shaft 12 may be opposed by a similar leg on the opposite side of the shaft. Stated differently, the shaft 12 may define a line of symmetry extending between the legs 22, such that an equal number of legs reside at equivalent positions on each side of the line. Referring to FIGS. 2a and 2f, for example, a plane may be said to extend through an axis defined by each shaft 12 in a direction running into and out of the page, and the legs 22 on one side of the plane may be a mirror image of the legs on the other side of the plane. As a result of this arrangement, when the clip 10 is applied to a valve leaflet, legs 22 will exert substantially equal amounts of pressure on each side of the leaflet tissue, enabling the clip 10 to maintain application or fold formed in the damaged mitral valve tissue.

Referring still to FIGS. 2a-f, each leg 22 may have a length extending from its point of connection 24 to its free end that is greater than the distance between the point of connection 24 and the first end 14 of the shaft 12. In other words, the length of each leg 22 may be greater than the length of shaft 12. Thus, in the folded or operative condition of the clip 10, the plurality of legs 22 may extend beyond the distal-most point of the barb 18 to grasp damaged mitral valve tissue distal to the barb. For example, with the point of connection 24 located at the second end 16 of the shaft 12 and the barb 18 located at the first end 14, the length of each leg 22 may be greater than the length of the shaft from the first end to the second end. Therefore, upon deploying the clip 10, the plurality of legs 22 may extend beyond the first end 14 of the shaft (and thus beyond the barb 18) to grasp the damaged mitral valve tissue. Alternatively, the length of each leg 22 may be less than the length of the shaft 12, if desired.

Each clip 10 may be formed from a shape memory material, such as Nitinol, and may be heat treated or heat set in a particular shape. Specifically, the clip 10, and thus the plurality of legs 22, may be constrained in a fixture, such as a mandrel or a mold, and a portion or all of the legs may be subjected to heat in a known process, causing the legs to "memorize" the shape of the mandrel or mold. This memorized shape may correspond to the use or deployed condition of the clip 10, as discussed in more detail below. As a result of this processing, if legs 22 are bent away from their memorized condition, upon entering the body of a patient and warming past a certain transition temperature, legs 22 may revert back to such memorized shape.

One or more of legs 22 may further include a puncturing member 28 formed on free end 26, such that the free end may puncture the mitral valve tissue when the clip 10 moves to its memorized shape. In a specific embodiment, the clip 10 may be formed from a flat sheet of material defining a plane and the puncturing member 28 may be arranged normal to the plane (e.g., into or out of the page for clips 10 of FIGS. 2a-2f).

The puncturing member 28 may further include its own barb formed on a portion thereof (not shown). With such a barb in place, the puncturing member 28 may puncture the leaflet tissue when the clip 10 moves to its deployed condition, thus establishing a secure connection between the barb (not shown) and the leaflet tissue.

Referring now to FIG. 3a, an exemplary delivery device for transcatheter gathering of heart valve leaflet tissue includes an elongated catheter assembly 34 adapted to be inserted through the apex of a human heart so that a distal portion 35 of the catheter assembly may reach the patient's mitral valve 1 for repair thereof.

The catheter assembly 34 may include a containment tube 40 disposed within an outer tube 39 and longitudinally slidable therein between a retracted position within the outer tube (FIG. 3a) and a deployed position in which a distal tip 41 of the containment tube protrudes distally beyond the distal end 43 of the outer tube (FIG. 3b). In a particular embodiment, the outer tube 39 may be made of one or more echogenic materials, so that the outer tube may be more easily visualized inside a patient using three-dimensional echocardiography.

Figure 4A:
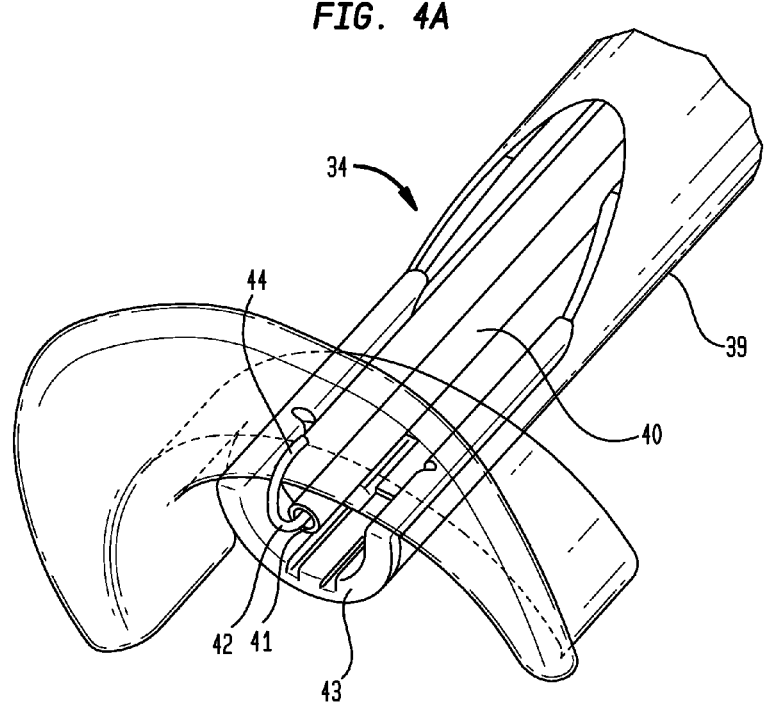
FIGS. 4a and 4b are a perspective view and a longitudinal cross-sectional view, respectively, of the distal portion of the device of FIG. 3a, shown with the hook deployed.
Figure 4B:
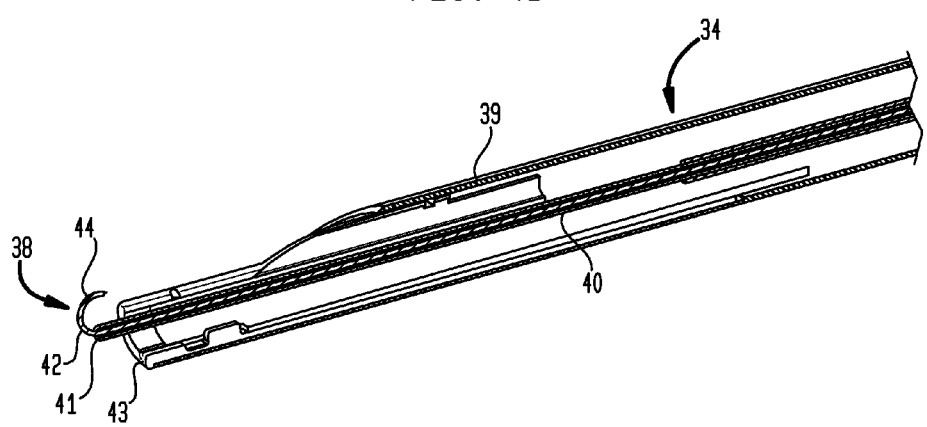

The catheter assembly 34 may further include a capture tool in the form of a grasping wire 38 that is longitudinally slidable within the containment tube 40 between a retracted position substantially entirely within the lumen of the containment tube (FIGS. 3a and 3b), and a deployed position in which a distal portion 42 of the grasping wire protrudes from the distal tip of the containment tube (FIGS. 4a and 4b). The grasping wire 38 may have a linear configuration when fully retracted within the containment tube 40 and the distal portion 42 thereof may assume the shape of a hook 44 when deployed from the containment tube. In that regard, the grasping wire 38 may be formed from a shape memory metal or a strong, resilient metal or polymer that will cause the hook 44 to form automatically when deployed.

Figure 5A:
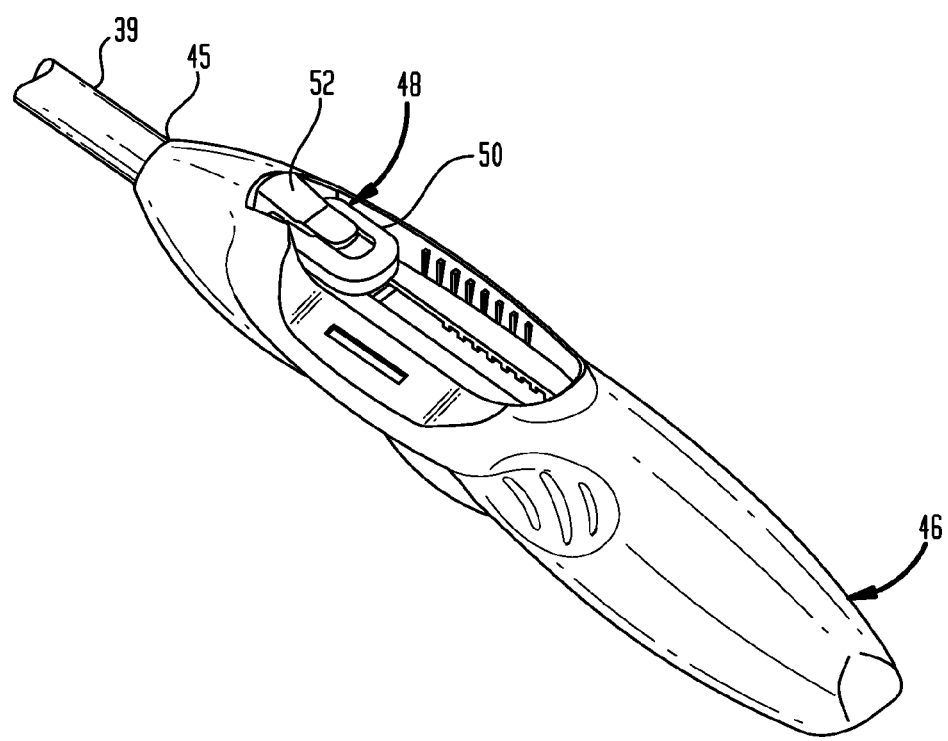
Figure 5B:
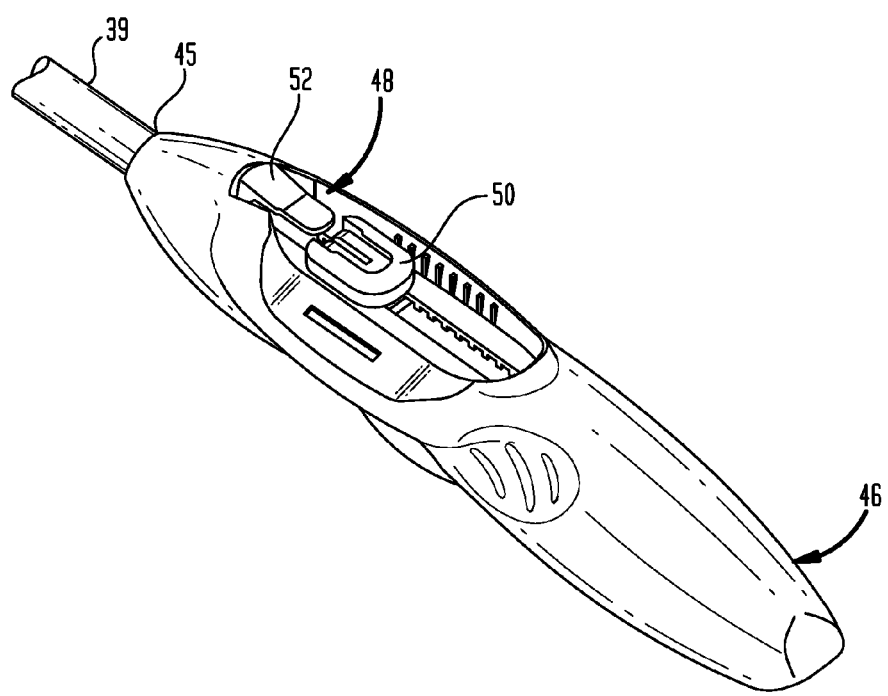
FIG. 5b is a perspective view of the handle of FIG. 5a, shown with the buttons positioned to correspond to the positions of the components of the device shown in FIGS. 4a and 4b.

Referring now to FIGS. 5a and 5b, the delivery device 32 may further include a handle 46 at the proximal end 45 of the outer tube 39. The handle 46 may include a button 48 for controlling the operation of the containment tube 40 and the grasping wire 38. The button 48 has a first portion 50 and a second portion 52 that are moveable longitudinally relative to the handle 46 and relative to one another. The first portion 50 is attached to the containment tube 40, such that sliding movement of the first portion in a proximal or distal direction results in a corresponding sliding movement of the containment tube. The second portion 52 is attached to the grasping wire 38, such that sliding movement of the second portion in a proximal or distal direction results in a corresponding sliding movement of the grasping wire. The containment tube 40 and the grasping wire 38 may be moved together by the simultaneous movement of the first and second portions of the button 48. Alternatively, the containment tube 40 and the grasping wire 38 may be moved independently of one another by moving one of the portions of the button 48 while the other portion remains stationary. For example, sliding the second portion 52 distally while the first portion 50 remains stationary advances the grasping wire 38 out from the containment tube 40, resulting in deployment of the hook 44 (FIG. 5b).

In some cases, a retaining arm (not shown) may also be included in the outer tube 39 of the catheter assembly 34 for retaining the clip 10 in a particular condition within the outer tube. In short, the retaining arm may be similar to any of the retaining arms described in U.S. Provisional Patent Application No. 61/438,446 ("the '446 application"), the disclosure of which is hereby incorporated by reference herein in its entirety. Thus, the retaining arm (referred to as retaining arm 50 in the '446 application) may include fingers (not shown) that overlie a portion of the clip 10 when situated within outer tube 39 and, when the fingers are retracted from overlying the clip, the clip may spring into its memorized shape. Indeed, as disclosed in the '446 application, a button (s) may be provided on handle 46 of catheter assembly 34 for moving the retaining mechanism and retracting the fingers thereof from over the clip 10. In a modification of the retaining arm described in the '446 application, it is contemplated that the retaining arm of the catheter assembly 34 may be movable in a distal direction, whereupon a portion of the retaining arm may engage the clip 10 (e.g., a proximal edge of the clip) to move the clip distally and at least partially out from the outer tube 39 of the assembly. Thus, the retaining arm may be configured to move the clip 10 distally within the catheter assembly 34, and may be operatively connected to the clip to also move the clip proximally, if desired.

To use the delivery device 32 for transcatheter gathering of heart valve leaflet tissue, a user may first position a clip 10 within the outer tube 39 of the catheter assembly 34. In this regard, when the clip 10 is loaded into outer tube 39, it will be biased toward its use condition. However, the clip will be moved to a more open condition and held in this restrained condition by the retaining arm of the delivery device 32. In the restrained condition, the plurality of legs 22 of the clip 10 may be curved or alternatively flat along the inner surface of the outer tube 39 and restrained from grasping the loose or billowed mitral valve tissue 1. When the clip 10 is deployed to the use condition, the legs 22 may be free to engage the loose leaflet tissue. In this regard, for example, the legs 22 may assume any of the configurations shown in FIGS. 10a-f to engage tissue.

In a particular embodiment, in the restrained condition the plurality of legs 22 may be positioned substantially in a C-shape within the outer tube 39 of the catheter assembly 34 (e.g., legs 22 may be arranged to form a C-shape extending into and out of the page in FIGS. 2a-f, such that the C-shape corresponds substantially to a portion of the inner surface of the outer tube). Thus, the C-shape of the clip 10 in the restrained condition may track a portion of the inner surface of the tube 39. Alternatively, the plurality of legs 22 in the restrained condition may travel along or adjacent to portions of the inner surface of the outer tube 39 but be flat. Stated differently, the legs 22 may remain flat (as opposed to curved), as shown in FIGS. 2a-f, and be bent into a V-shape within the outer tube 30. The fingers of the retaining arm may then be positioned over the legs 22 along the inner surface of the tube 39 to keep the clip 10 in its restrained (e.g., C-shaped or V-shaped) condition. In addition, the barb 18 of shaft 12 (or at least one of the barbs if clip 10 has multiple shafts), may be arranged to extend towards the distal end 43 of the outer tube 39. Thus, in the restrained condition, the barb may extend along the inner surface of the outer tube 39 towards distal end 43, and the legs 22 of the clip 10 may be restrained substantially in a C-shape or V-shape by the fingers of the retaining arm. Further, the clip 10 may be placed in its restrained condition adjacent the distal end 43 of the outer tube 39 so that the clip can be easily deployed.

With the clip 10 positioned in the outer tube 39 in its restrained condition, the distal portion 35 of the catheter assembly 34 may be inserted into a patient through the apex of the heart, for example, into the left ventricle, so that the distal portion extends between the posterior leaflet 2 and the anterior leaflet 3 of the mitral valve 1. As shown in FIG. 3a, the distal end 43 of the outer tube 39 may be disposed approximately at the coaption line 5 of the mitral valve 1, and may be guided into this position using the assistance of three-dimensional echocardiography or another technique to visualize the outer tube or other components of the catheter assembly 34.

Referring to FIG. 3b, the containment tube 40 may then be deployed by sliding the first and second portions 50 and 52 of the button 48 together distally from an initial position to a deployed position. The distal movement of the button 48 moves the tip of the containment tube 40 beyond the distal end 43 of the outer tube 39, such that the tip extends above the coaption line 5. While sliding the containment tube 40 within the outer tube 39, the containment tube may travel between the legs 22 of the clip 10 situated in the outer tube 39 (e.g., due to the clip's C-shape or V-shape along the inner surface of tube 39). As such, the clip 10 does not interfere with movement of the containment tube 40 within the outer tube 39.

The hook 44 may then be deployed to an extended position by sliding the second portion 52 of the button 48 distally relative to the first portion 50 from an initial position (FIG. 5a) to a deployed position (FIG. 5b). Referring to FIGS. 4a-4b, the distal movement of the second portion 52 relative to the first portion 50 moves the distal portion 42 of the grasping wire 38 out of the containment tube 40. No longer being constrained by the containment tube 40, the distal portion 42 of the grasping wire 38 may assume the curved shape of the hook 44.

Figure 7A:
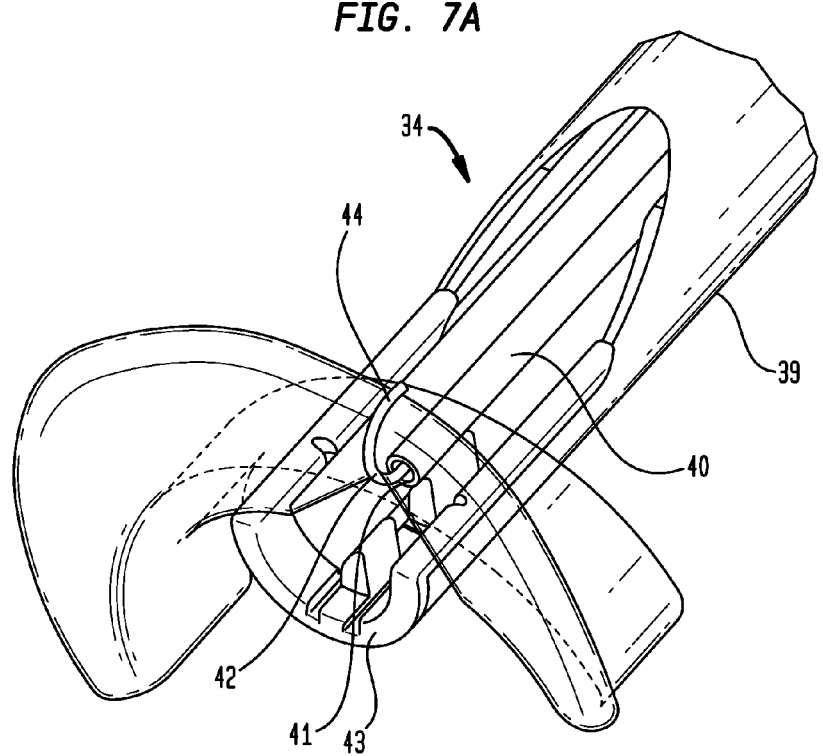
FIG. 7a is a perspective view of the distal portion of the device of FIG. 3a, shown with the hook in the partially retracted position.
Figure 7B:
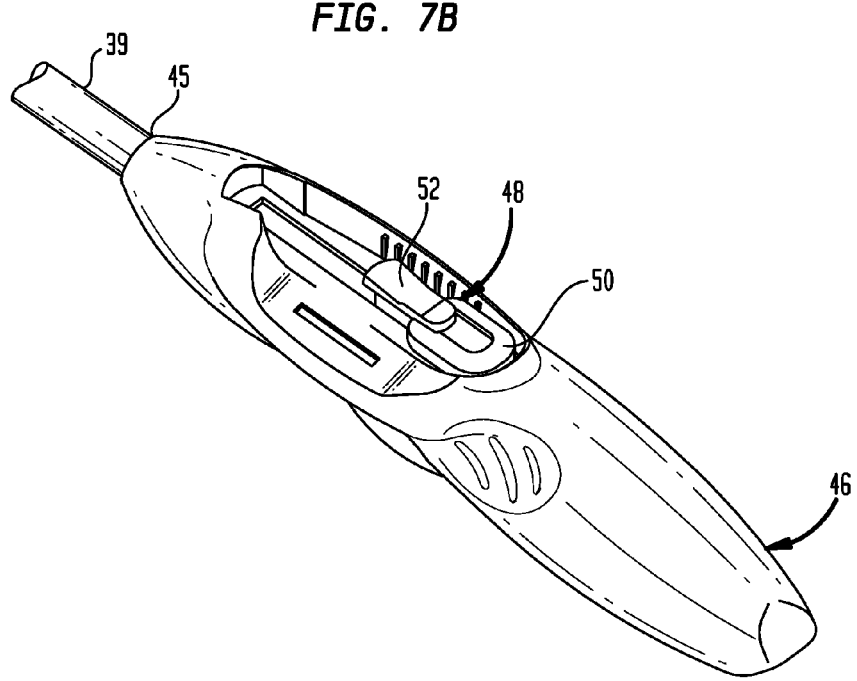

The hook 44 may be partially retracted against the tissue of the posterior leaflet 2 by sliding the first and second portions 50 and 52 of the button 48 together proximally (FIG. 7b). The proximal movement of the button 48 partially retracts both the containment tube 40 and the grasping wire 38, such that the hook 44 engages the upper surface 6 of the posterior leaflet 2 and pulls tissue of the leaflet at least partially towards the distal end 43 of the outer tube 39. A secure connection is therefore established between the hook 44 and the grasped tissue.

With the leaflet tissue securely held by the hook 44, the delivery device 32 may be operated to deploy the clip 10 onto the gathered tissue (i.e., into the use condition). In this regard, the retaining arm of the catheter assembly 34 may be used to advance the clip 10 (and thus the barb 18) towards the distal end 43 of the outer tube 39. Then, with the leaflet tissue secured by the hook 44 adjacent distal end 43, the clip 10 may be advanced until barb 18 protrudes from the distal end 43 of the outer tube 39 to puncture the leaflet tissue. At this stage, the legs 22 of the clip 10 may still be maintained in their restrained condition (e.g., C-shaped or V-shaped) by the fingers of the retaining arm. Subsequently, the entire catheter assembly 34 may be retracted to create a plication or fold in the leaflet tissue 1, or just the containment tube 40 and hook 44 may be retracted to achieve the same effect. To deploy the clip 10 to its use condition around the plication, the fingers of the retaining arm may be retracted proximal of the legs 22 of the clip to release the legs for movement to their use condition.

Figure 10A:
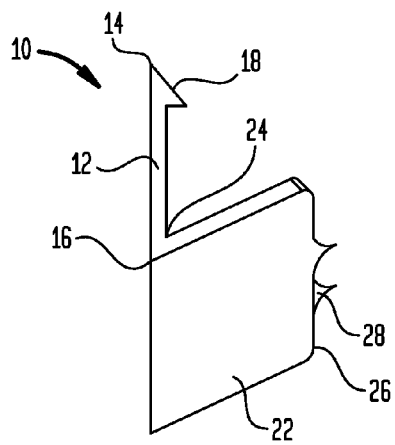
FIGS. 10a-f are various perspective views of certain of the clips shown in FIGS. 2a-f in their deployed or use condition.
Figure 10B:
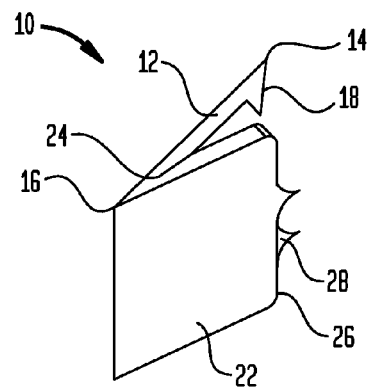
Figure 10C:
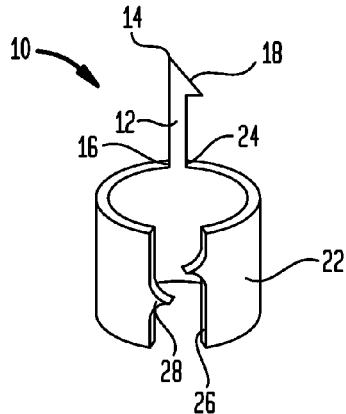
Figure 10D:
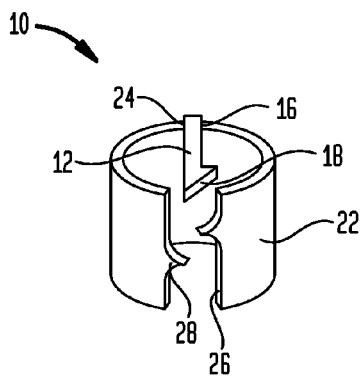

In the use condition, the plurality of legs 22 may be released from the aforementioned C-shape to curl about one another and form a complete or near-complete circle. The legs 22 may also fold past one another when situated in a complete circle (although not shown in FIGS. 10a-f). Alternatively, if in a V-shape within the outer tube 39, the legs 22 may simply move or close about one another, such that the space between the legs 22 is lessened. A clip 10 with legs 22 folded from a C-shape to curl about one another and form a circle or near-circle is shown in FIGS. 10c-d, while a clip 10 folded from a V-shape so that the legs 22 move towards one another is shown in FIGS. 10a-b. When moving to the use condition, the legs 22 may also fold by about 90° relative to the shaft 12 of the clip, preferably at or near point of connection 24 or the second end of the shaft, so as to be better positioned to grasp the tissue held by barb 18. This is exemplified by the transition from FIGS. 10a and 10c to FIGS. 10b and 10d, respectively. In other words, referring to FIGS. 2a-f, the legs 22 may fold by about 90° out of the plane of the page, preferably about the point of connection 24 between the legs and the shaft 12 or at the second end 16 of the shaft (e.g., towards the barb 18 that is already punctured through tissue 1). Thus, in transitioning to the use condition, the following motions may occur: (1) closing of the legs 22 to form a circle or near-circle, in the case of a C-shaped clip 10 (e.g., FIGS. 10c-d); (2) movement of the legs 22 towards one another, in the case of a V-shaped clip (e.g., FIGS. 10a-b); and (3) simultaneous folding of the legs, in either case, by about 90° at or near the second end 16 of the shaft 12 to place the clip 10 in a condition in which it grasps tissue 1. Again, this latter movement is exemplified by the transition from FIGS. 10a and 10c to FIGS. 10b and 10d, respectively.

In embodiments in which the legs 22 may contain a puncturing member 28, the aforementioned movement of legs 22 towards one another or to form a circle or near-circle may also cause the puncturing member 28 to puncture tissue. Thus, in such embodiments, the clip 10 may be more securely retained on tissue 1.

After securing the clip 10 to the leaflet tissue, as discussed above, the hook 44 of the grasping wire 38 may be retracted into the containment tube 40 of the catheter assembly 34 by sliding the second portion 52 of the button 48 proximally relative to the first portion 50. This action causes the hook to straighten as the grasping wire 38 retracts into the containment tube 40. The distal portion 42 of the grasping wire 38 may thus assume its initial substantially linear shape upon retraction into the containment tube 40. Upon retraction of the hook 44 into the containment tube 40, some portion of the grasping wire 38 may also travel between several legs 22 of the deployed clip 10 (e.g., so as to not interfere with the clip during retraction of the hook 44 and the grasping wire 38). Stated differently, since in some cases the containment tube 40 may be situated such that the grasping wire 38 extends between several legs 22 of the clip 10 during deployment thereof, the grasping wire and the hook 44 may be retracted through the legs of the clip so as to not interfere therewith once deployed. Subsequently, the containment tube 40 may be retracted into the outer tube 39 by sliding the first portion 50 and second portion 52 of the button 48 simultaneously in the proximal direction.

Culminating the procedure, the device 32 may be withdrawn from the body of the patient through the apex of the heart, leaving the clip 10 intact. The aforementioned procedure may be repeated, if necessary, to apply one or more additional clips 10 onto the mitral valve leaflet until an adequate tightening of the leaflet tissue has been achieved.

In the deployment of clips 10 having multiple shafts 12, as is the case with some of the clips depicted in FIGS. 2a-f, the method would progress in a substantially similar manner. In the restrained condition of such clips, one of the shafts 12 would extend towards the distal end 43 of the outer tube 39, as described above, while the other shaft would extend towards the proximal end 45 of the outer tube. In other words, referring to FIGS. 2a-f, in a multi-shaft scenario the lower shaft 12 in the figures may be situated within outer tube 39 so as to face proximal end 45, while the upper shaft 12 in the figures may face distal end 43. At the same time, the legs 22 may be restrained in the C-shaped or V-shaped condition (i.e., C-shaped or V-shaped into and out of the plane of the page in FIGS. 2a-f) within the outer tube 39, as described above.

Figure 10E:
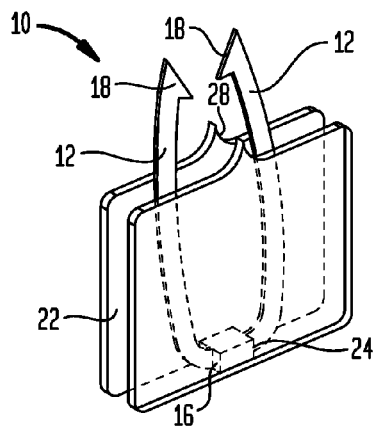
Figure 10F:
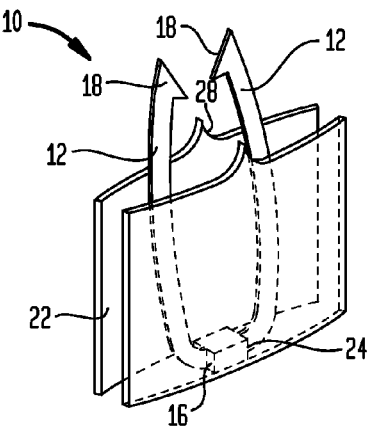

Then, in the use condition the legs 22 may move towards one another or collapse into a circle or near-circle, as detailed previously, while also folding about 90° out of the plane of the page in FIGS. 2a-f. A clip 10 with multiple shafts 12 in such a use condition, for example, is shown in detail in FIGS. 10e-f. The salient difference in this multi-shaft scenario, for the use condition, would be the folding of the lower shaft 12. Indeed, the lower shaft 12 in FIGS. 2a-f may also fold by about 90° relative to the legs 22 when in the use condition, thereby situating the lower shaft 12 roughly parallel to the upper shaft 12 (which is inserted into tissue 1 prior to the clip 10 being placed in the use condition). The shafts 12 in their parallel condition are shown in FIGS. 10e-f. Thus, the method of insertion of a clip 10 having multiple shafts 12 may progress substantially as described above for one shaft, with the additional step of the second shaft folding relative to the legs 22 so as to be substantially parallel to the first shaft. In this folded condition, the barb 18 on the free end of the second shaft 12 may pierce tissue 1 at a spaced distance from the first shaft, further securing clip 10 into the tissue.

Figure 9A:
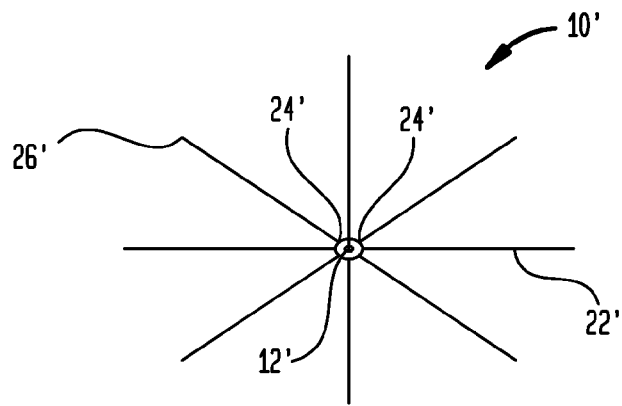
Figure 9B:
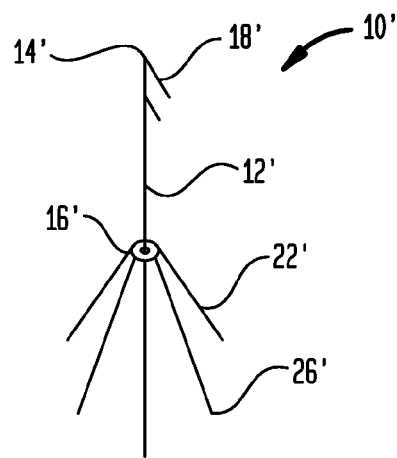
FIGS. 9b-c are side views of the clip of FIG. 9a shown with the legs in their restrained and use conditions.
Figure 9C:
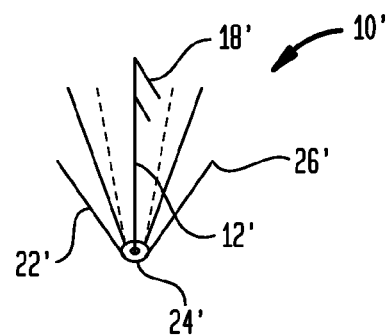

A variant of the aforementioned clips 10 is also contemplated, as shown in FIGS. 9a-c. There, like numerals refer to like elements, except that the reference numbers are expressed in primes. Thus, as shown in FIGS. 9a-c, the clip 10' may include a shaft 12' having first and second ends 14', 16', a barb 18' on the first end 14' of the shaft, and a plurality of legs 22' connected to the shaft at a point of connection 24'. The legs 22' may also have a free end 26' that may be bent or deformed, as with clips 10. The legs 22' of the clip 10' may be arranged equally on either side of the shaft 12' so as to grasp tissue efficiently. This is the same as with clips 10, and thus, many characteristics of clips 10 and 10' are similar.

As shown in FIG. 9a, the shaft 12' of the clip 10' may be centered with respect to the legs 22'. Further, the restrained and use conditions of the clip 10' may be different from clips 10. In the use condition of clip 10', the plurality of legs 22' may form an array encircling shaft 12' and pointing in substantially the same direction as the shaft, as shown in FIG. 9c. In the restrained condition, on the other hand, the legs 22' will be oriented in substantially the opposite direction to shaft 12', as shown in FIG. 9b. Because of these differences in the restrained and use conditions of clip 10', a different insertion method is warranted. Such method is described in more detail below.

Prior to discussing this alternate method, it must be noted that the delivery device 32 may be slightly modified to accommodate the different configuration of the clip 10'. As clip 10' in the restrained condition has a generally linear profile, legs 22' may be held in the restrained condition by the inner surface of outer tube 39. Accordingly, there is no need for this modified delivery device 32 to include a retaining arm with fingers, as described above. Moreover, referring to FIG. 6, the modified delivery device 32 may include an inner tube or pusher 54 that advances the clip 10' towards the distal end 43 of the outer tube 39. The pusher 54 may be displaced through the use of a button or actuator (not shown) on handle 46. For example, a button, similar to the button 48, may be coupled with the pusher 54 such that movement of the button in a proximal or distal direction results in a corresponding movement of the pusher. The pusher 54 may have a distal surface 56 shaped and sized to contact a portion of the clip 10' to push the clip distally. In other words, the distal surface 56 of the pusher 54 may only contact the clip 10' and not be connected thereto, such that movement of the pusher distally results in movement of the clip toward the distal end 43 of the outer tube 39, but proximal movement of the pusher does not result in proximal movement of the clip. Alternatively, the pusher 54 may be operatively connected to the clip 10' so that movement of the pusher in a proximal or distal direction results in a corresponding movement of the clip either proximally or distally.

The modified delivery device 32 may employ multiple containment tubes 40 and corresponding grasping wires 38 and hooks 44, as opposed to one containment tube 40 and one grasping wire 38, as in the delivery device described previously.

To use the modified device 32 for transcatheter gathering of heart valve leaflet tissue, a user may first collapse a clip 10' by bending its legs 22' away from its shaft 12' to minimize the transverse cross-section of the clip. The collapsed clip 10' may then be inserted into the distal end 43 of the outer tube 39 of the catheter assembly 34, such that the barb 18' faces towards the open distal end 43 of the outer tube, and the legs 22' face towards the proximal end 45 of the outer tube. This corresponds to the restrained condition of the clip 10', as shown in FIG. 6. Once the clip 10' is loaded into the outer tube 39, the outer tube may restrain the legs 22' and prevent them from moving to the use condition, that is, until the clip is deployed from the outer tube by a pusher 54 or other mechanism, allowing the legs to freely move into their use condition. As an alternative to the above, the clip 10' may be preloaded in the outer tube 39 of the catheter assembly 34 by the manufacturer (e.g., in its restrained condition).

Figure 8A:
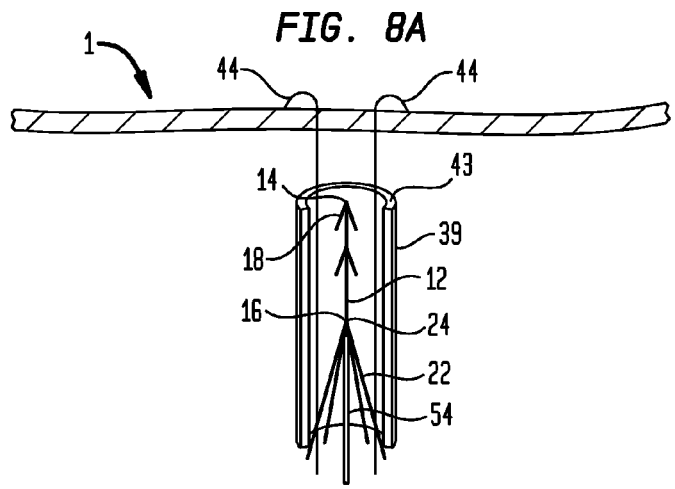
Figure 8B:
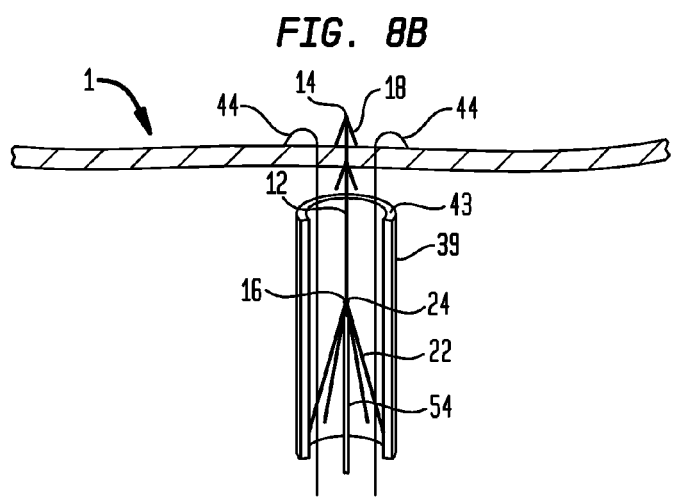

The subsequent steps of the method may progress substantially as described above in connection with the deployment of clips 10, except that no retaining arm is utilized, and multiple grasping wires 38 with hooks 44 may be employed. In this regard, referring to FIGS. 8a-e, once the outer tube 39 of the catheter assembly 34 is situated near the coaption line 5 of mitral valve 1, one or more grasping wires 38 may be deployed in the manner described previously (e.g., through actuation of button 48) so that the hooks 44 on the distal ends of the grasping wires may grasp tissue and pull the same towards the distal end 43 of the outer tube. Then, as shown in FIG. 8b, pusher 54 may be advanced distally against the clip 10'. The legs 22' of the clip 10' may extend past the tip of the pusher 54 towards the proximal end 45 of the outer tube 39 so as to not interfere with the pusher as it forces the clip distally. As the clip 10' advances, the barb 18' thereof may move towards and out from the distal end 43 of the outer tube 39. With the hooks 44 holding the leaflet tissue at or near the distal end 43 of the outer tube 39, further advancement of the clip 10' may force barb 18' into and through the tissue of the leaflet, as shown in FIG. 8b.

Figure 8C:
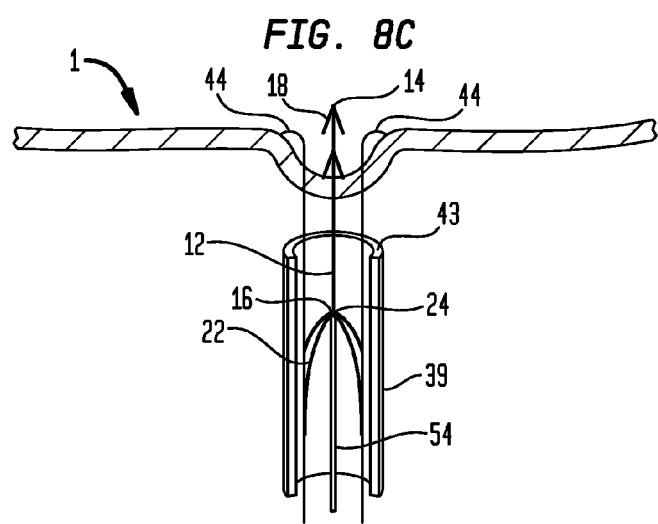
Figure 8D:
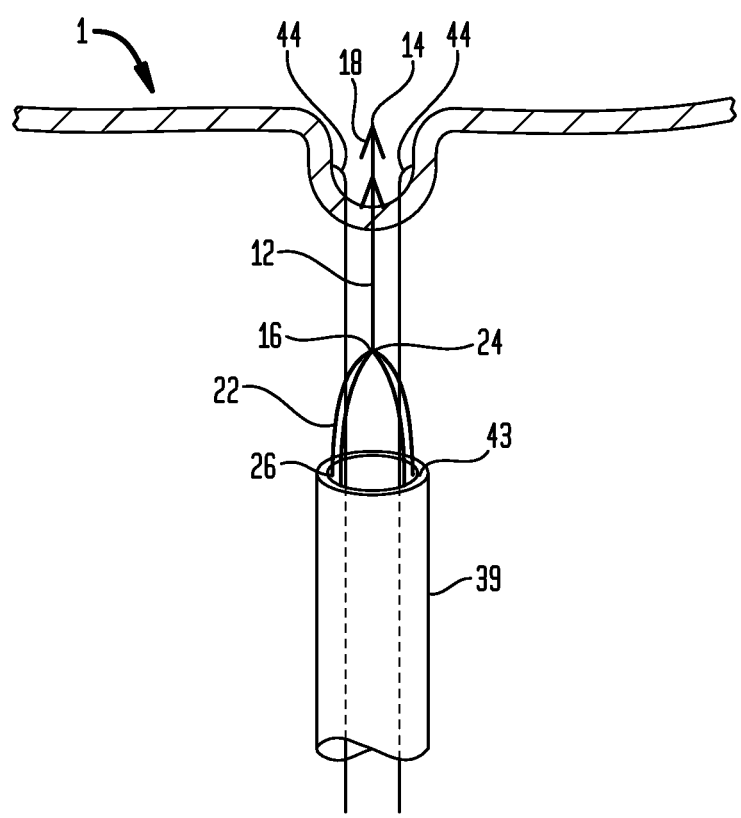

Puncturing the barb 18' through the leaflet tissue firmly secures the clip 10' to the tissue. The entire delivery device 32 may then be retracted, with the hooks 44 and barb 18' pulling on the tissue to create a plication or fold in the tissue (FIG. 8c). Once an adequate plication has been formed, the outer tube 39 of the catheter assembly 34 may be retracted proximally relative to the pusher 54 and the clip 10' until the distal end 43 of the outer tube 39 is proximal of the free ends 26' of the legs 22' (shown in progress in FIG. 8d). At this juncture, clip 10' is fully deployed from outer tube 39. No longer restrained by outer tube 39, the legs 22' of clip 10' may spring into the use condition, with some of the legs on each side of the plication (FIG. 8e). In other words, the legs 22' may fold from their restrained condition in which they extend from the points of connection 24' away from the first end 14' of the shaft 12', to the use condition in which they extend from the points of connection towards the first end having barb 18'. Thus, legs 22' may fold from their restrained condition within outer tube 39 to a condition in which their free ends 26' point towards the leaflet tissue (i.e., the use condition).

When deployed to the use condition, the legs 22' may engage the leaflet tissue 1 and secure the plication therein to shorten the tissue and alleviate its floppy or billowed characteristics. In some embodiments, the plurality of legs 22' may partially or completely surround the barb 18' to provide for even greater securing of the clip 10' to the leaflet tissue. In other embodiments, the free end 26' of at least some legs 22' may also include a puncturing member (not shown), and the puncturing member may puncture into the leaflet tissue when the legs are situated in the use condition. These embodiments create an even more secure attachment of the clip 10' to the leaflet tissue. Once clip 10' has been deployed, the modified delivery device 32 may be used to deploy one or more additional clips as desired. Following the deployment of the desired number of clips, the modified delivery device 32 may be removed from the patient in the same manner as the delivery device described above.

In the devices shown in the figures, particular structures are shown that are adapted to gather, secure, and repair heart valve leaflet tissue. The invention also contemplates the use of alternative structures for such purposes, including structures having different lengths, shapes, and configurations. For example, although a grasping wire 38 forming a hook 44 is shown and described for capturing and gathering the leaflet tissue, other types of devices may be used for this purpose, including, for example, a pincer-like structure such as a clamp.

In another example, although the catheter assembly 34 is described as being controllable by the movement of a particular button 48 of a handle 46, any mechanisms that are adapted to control the movement and deployment of the containment tube 40, grasping wire 38, clips 10, 10', the retaining arm, and/or pusher 54 may be used. Furthermore, although the grasping wire 38 is shown as forming a hook 44, the distal portion of the grasping wire may have any shape or configuration that may be adapted to grasp a target portion of valve leaflet tissue and help to capture such tissue adjacent the outer tube 39, such that a clip may be applied to the captured tissue.

Moreover, while the barb has been described as being located on the first end of the shaft, any suitable location for the barb on the shaft is contemplated, including a location at or between the first and second ends of the shaft. The shaft may also have multiple barbs instead of having only one such barb to better secure the shaft to the leaflet tissue. It is also contemplated that multiple barbs may be provided in connection with clips having multiple shafts.

In yet another example, although the plurality of clip legs are described as being formed from a shape memory material, the legs may alternatively be formed from any suitable material allowing the legs to achieve the multiple conditions described, such as, for example, a spring metal or a strong, resilient metal or polymer. Also, although the clips are shown as including at most eight (8) legs, it is contemplated that the clips may include any number of legs as desired.

Moreover, even though, in one embodiment, the arrangement of the clip legs has been described such that an equal number of legs may be disposed on each side of the shaft, it is contemplated that the number of legs on each side of the shaft may be different.

What is more, the transition from FIGS. 10a and 10c to 10b and 10d, respectively, is described above as exemplifying the folding of the legs 22 of the clip 10 90° relative to the shaft 12. Yet, FIGS. 10a and 10c may also represent an alternate use condition for the clip 10. In particular, it is contemplated that in one use condition the legs 22 may not fold 90° relative to the shaft 12, but rather may remain in the configuration shown in FIGS. 10a and 10c. As an example, with the clip 10 situated in the outer tube 39 in its restrained (e.g., C-shaped or V-shaped) condition, the barb 18 may be utilized to puncture tissue at or near the distal end 43 of the outer tube 39. Then, as described in detail in the '446 application, for example, the tissue may be pulled past the distal end 43 of the outer tube 39 via retraction of the hook portion 44 of the grasping wire 38 and/or its containment tube 40. The tissue may be pulled by an amount sufficient to place it near the open portion of the outer tube 39, as shown, for example, in FIG. 7*a*. The legs 22 of the clip 10 may then be deployed to a use condition in which they move towards one another or fold to form a circle or near-circle, as detailed above and shown in FIGS. 10*a* and 10*c*. Due to the fact that tissue is at the open end of the outer tube 39, the legs 22 may therefore grasp the tissue as they move towards one another or form a circle or near-circle, while the barb 18 may be securely punctured through a portion of tissue distal of the legs 22. In this manner, the clip 10 may be placed in a use condition in which its legs 22 do not fold by about 90° relative to the shaft 12, but rather remain in the configuration shown in FIGS. 10*a* and 10*c*.

Although catheter assembly 34 has been described as having a single containment tube 40, the catheter assembly 34 may include multiple containment tubes arranged within the outer tube 39, each having its own grasping wire 38, as described with reference to FIGS. 8*a-e*. Alternatively, each containment tube 40 may have multiple grasping wires 38, or the catheter assembly may be provided with one containment tube having multiple grasping wires 38 therein. Where the catheter assembly includes multiple containment tubes 40, the containment tubes may be operated in a manner similar to the operation of the one containment tube described previously. Thus, each containment tube 40 may be operatively connected to a button similar to button 48 to both: (1) move the containment tube proximally or distally; and (2) deploy or retract a grasping wire(s) 38 within the containment tube. In a variant hereof, a single button 48 may be used to simultaneously operate all of the containment tubes 40, and to deploy all of the grasping wires 38 therefrom.

By virtue of situating multiple containment tubes 40 within the outer tube 39 of the catheter assembly 34, each containment tube having one or more grasping wires 38, multiple hooks 44 may be employed. Thus, during operation, the multiple containment tubes 40 and hooks 44 may be deployed to grasp tissue, and once the clip has been deployed around such tissue, the tubes and hooks may be retracted to leave the clip applied to the tissue.

The procedure for repairing a mitral valve leaflet has been described above as employing a device 32 having only a single clip disposed within the outer tube 39 of catheter assembly 34. However, it is also contemplated that multiple clips may be positioned in the outer tube 39 of the catheter assembly 34 for sequential or simultaneous deployment onto the leaflet tissue. Thus, instead of repeating the entire procedure described above to deploy multiple clips, such clips may be pre-loaded into the catheter assembly 34 and deployed one at a time without having to remove device 32 from the patient between each clip deployment.

Although the various delivery devices and clips have been described herein in connection with tightening the posterior leaflet of a mitral valve, all of the delivery devices and clips may be used on other heart valve leaflets, such as the anterior leaflet of the mitral valve, or on any other tissue of the body for which a reduction in the length or area of the tissue would be beneficial.

Additionally, while particular delivery devices 32 have been described herein, it is contemplated that any number of different delivery devices may be used to deploy the clips. Specifically, while the delivery devices 32 are, in many respects, similar to that disclosed in the '446 application, it is contemplated that other delivery devices may be used to deploy the clips.

Although the invention herein has been described with reference to particular embodiments in which the catheter assembly is inserted into the patient via an introducer and through the apex of the heart (i.e., transapical insertion), it is to be understood that the invention contemplates embodiments in which the catheter assembly is inserted through the wall of the heart at a different location, or extends through a portion of the vasculature of the patient to reach the heart, for example, through a transfemoral or subclavian artery or vein. In such embodiments, some of the device components may have to be oriented in a different direction to that described herein and some of the components may need to be flexible. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A clip for attachment to tissue of a heart valve leaflet, comprising:
    a shaft extending in a longitudinal direction between first and second ends;
    a sharpened tip on the first end of the shaft; and
    a plurality of legs, each leg having one end connected to the shaft at a point of connection spaced from the sharpened tip and extending in a length direction from the one end to a free end, the plurality of legs having an initial condition in which the plurality of legs and the shaft lie in a first plane, the plurality of legs being deformable from the initial condition to an at least partially open condition and being biased from the at least partially open condition to a use condition for application to the leaflet tissue, the plurality of legs in the at least partially open condition extending from the shaft toward one side of the first plane and the plurality of legs in the use condition extending from the shaft toward the one side of the first plane and having their free ends positioned adjacent one another, and the first end of the shaft in the use condition being positioned adjacent the free ends of the plurality of legs.

2. The clip of claim 1, wherein the plurality of legs are at least partially formed of a shape memory material.

3. The clip of claim 1, further comprising a barb disposed on the shaft.

4. The clip of claim 1, wherein a second plane orthogonal to the first plane extends through the shaft and the plurality of legs are connected to the shaft such that an equal number of legs are disposed on each side of the second plane.

5. The clip of claim 1, wherein each leg has a length between the one end and the free end that is greater than the distance between the point of connection of the leg to the shaft and the sharpened tip.

6. The clip of claim 1, wherein in the use condition the legs form an angled structure disposed on opposite sides of a longitudinal axis and the shaft is disposed at a transverse angle to the longitudinal axis.

7. The clip of claim 1, wherein in the use condition the legs form a structure that curves about a longitudinal axis and the shaft is disposed at a transverse angle to the longitudinal axis.

8. The clip of claim 1, wherein at least one of the plurality of legs includes a puncturing member adapted to puncture the leaflet tissue upon applying the clip to the tissue.

9. The clip of claim 8, wherein the puncturing member includes a barb.

10. The clip of claim 1, further comprising a sharpened tip on the second end of the shaft.

11. The clip of claim 10, wherein the shaft has a first portion extending from the point of connection to the first end and a second portion extending from the point of connection to the second end, and in the use condition the legs form a structure that curves about a longitudinal axis, the first portion of the shaft is disposed at a transverse angle to the longitudinal axis and the second portion of the shaft is disposed at a transverse angle to the longitudinal axis.

12. A system for attaching a clip to tissue of a heart valve leaflet, comprising:
    a delivery device including a catheter assembly extending in a longitudinal direction; and
    a clip contained in the delivery device for attachment to the leaflet tissue, the clip including:
        a shaft extending in a longitudinal direction between first and second ends;
        a sharpened tip on the first end of the shaft; and
        a plurality of legs, each leg having one end connected to the shaft at a point of connection spaced from the sharpened tip and a free end, the plurality of legs having an initial condition in which the plurality of legs and the shaft lie in a plane,
    wherein the clip is restrained in the delivery device in an at least partially open condition and is biased to move to a use condition upon deployment from the delivery device, the plurality of legs in the at least partially open condition extending from the shaft toward one side of the plane and the plurality of legs in the use condition extending from the shaft toward the one side of the plane and having their free ends positioned adjacent one another, and the first end of the shaft in the use condition being positioned adjacent the free ends of the plurality of legs.

13. The system of claim 12, further comprising a capture tool slidable in the catheter assembly between a retracted position and an extended position, the capture tool including a grasping member operable to grasp the leaflet tissue.

14. The system of claim 13, wherein the grasping member is a wire slidably disposed in a containment tube, the wire being made from a shape memory material.

15. The system of claim 13, wherein a distal portion of the grasping member changes from a substantially linear shape to a hook shape upon extension of the grasping member from the catheter assembly.

16. A transcatheter method of gathering tissue, the method comprising:
    inserting an elongated catheter assembly to a position adjacent the tissue, the catheter assembly extending in a longitudinal direction and including a capture tool and a clip as claimed in claim 1, the capture tool being moveable between a retracted position and an extended position in which a portion of the capture tool protrudes from a distal end of the catheter assembly;
    moving the capture tool from the retracted position to the extended position;
    engaging the capture tool with the tissue; and
    deploying the clip from the distal end of the catheter assembly, whereupon the sharpened tip punctures the tissue and the plurality of legs move from the at least partially open condition to the use condition about the tissue.

17. The method of claim 16, wherein the capture tool includes a grasping wire slidably disposed in a containment tube, the method further comprising sliding a distal portion of the grasping wire out from the containment tube so that the distal portion of the grasping wire changes from a substantially linear shape to a hook shape.

18. The method of claim 17, wherein the catheter assembly further includes a retaining arm movable between a distal position for retaining the plurality of legs in the at least partially open condition and a proximal position for releasing the plurality of legs, and the step of deploying the clip includes moving the retaining arm from the distal position to the proximal position, whereupon the plurality of legs move to the use condition about the tissue.

19. The method of claim 17, wherein the plurality of legs are at least partially formed of a shape memory material.

20. The method of claim 17, wherein the deploying step includes pushing the clip from the catheter assembly with a pushing member slidably disposed in the catheter assembly.

* * * * *